(12) United States Patent
Ohira et al.

(10) Patent No.: US 9,103,780 B2
(45) Date of Patent: Aug. 11, 2015

(54) PRETREATMENT DEVICE FOR DISSOLVED IONS ANALYSIS AND DISSOLVED ION ANALYSIS SYSTEM

(75) Inventors: Shin-Ichi Ohira, Kumamoto (JP); Kei Toda, Kumamoto (JP); Purnendu K. Dasgupta, Arlington, TX (US)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 124 days.

(21) Appl. No.: 13/990,984

(22) PCT Filed: Aug. 30, 2011

(86) PCT No.: PCT/JP2011/069567
§ 371 (c)(1),
(2), (4) Date: Aug. 20, 2013

(87) PCT Pub. No.: WO2012/073566
PCT Pub. Date: Jun. 7, 2012

(65) Prior Publication Data
US 2013/0327647 A1    Dec. 12, 2013

(30) Foreign Application Priority Data
Dec. 1, 2010   (JP) .................................. 2010-268404

(51) Int. Cl.
*G01N 1/38*   (2006.01)
*G01N 1/40*   (2006.01)
(Continued)

(52) U.S. Cl.
CPC ............ *G01N 27/44756* (2013.01); *G01N 1/38* (2013.01); *G01N 1/4005* (2013.01);
(Continued)

(58) Field of Classification Search
CPC . G01N 1/38; G01N 1/4005; G01N 2001/381; G01N 2001/383; G01N 2001/386; G01N 2001/4011; G01N 2001/4016; G01N 2001/4038
USPC .......................................................... 436/178
See application file for complete search history.

(56) References Cited

U.S. PATENT DOCUMENTS 3,582,488 A * 6/1971 Zeineh .......................... 204/544
5,861,097 A * 1/1999 Schafer et al. ................. 210/635
(Continued)

FOREIGN PATENT DOCUMENTS

EP          0820804      * 1/1998
JP          64-10162       1/1989
(Continued)

OTHER PUBLICATIONS

International Search Report mailed Oct. 4, 2011 in International (PCT) Application No. PCT/JP2011/069567.
(Continued)

*Primary Examiner* — Keith Hendricks
*Assistant Examiner* — Salil Jain
(74) *Attorney, Agent, or Firm* — Wenderoth, Lind & Ponack, L.L.P.

(57) ABSTRACT

A pretreatment device 10 for analysis of dissolved ions, which comprises: a sample solution flow channel 11 through which a sample solution containing dissolved ions flows; an acceptor solution flow channel 13 which is arranged adjacent to the sample solution flow channel 11 so as to intercalate a dialysis membrane 12 between the acceptor solution flow channel 13 and the sample solution flow channel 11; a pair of electrodes 14a, 14b which are so arranged as to intercalate the sample solution flow channel 11 and the acceptor solution flow channel 13 therebetween, wherein one of the pair of electrodes 14a, 14b is provided on the sample solution flow channel 11, and the other one of the pair of electrodes 14a, 14b is provided on the acceptor solution flow channel 13; a direct current power source 5 which enables the generation of a predetermined potential difference between the electrodes 14a, 14b; and an electrode separator 15 provided between the dialysis membrane 12 and an inside surface of the electrode provided on the acceptor solution flow channel 13.

9 Claims, 13 Drawing Sheets

(51) Int. Cl.
*G01N 1/28* (2006.01)
*G01N 27/447* (2006.01)

(52) U.S. Cl.
CPC .... *G01N2001/381* (2013.01); *G01N 2001/383* (2013.01); *G01N 2001/4016* (2013.01); *G01N 2001/4038* (2013.01)

(56) References Cited

U.S. PATENT DOCUMENTS

| | | | | |
|---|---|---|---|---|
| 6,395,233 | B1 * | 5/2002 | Diamond et al. | 422/527 |
| 7,001,550 | B2 * | 2/2006 | van Reis | 264/48 |
| 2005/0092666 | A1 * | 5/2005 | Wilson | 210/136 |

FOREIGN PATENT DOCUMENTS

| | | |
|---|---|---|
| JP | 64-12254 | 1/1989 |
| JP | 64-12255 | 1/1989 |
| JP | 6-125985 | 5/1994 |
| JP | 7-231935 | 9/1995 |
| JP | 2004-286665 | 10/2004 |

OTHER PUBLICATIONS

Shin-Ichi Ohira et al., "Ion transfer from sample matrix by means of electrophoretic behavior under the electric fields", The Japan Society for Analytical Chemistry, p. 199, Sep. 1, 2010, together with English translation thereof.

Kenta Hisahara et al., "Simultaneous and separately cation and anion extraction from sample solution with 5 thin solution layer device", The Japan Society for Analytical Chemistry, p. 402, Sep. 1, 2010, together with English translation thereof.

Brian De Bora et al., "On-line dialysis as a sample preparation technique for ion chromatography", Journal of Chromatography A, 919, pp. 59-65, 2001.

* cited by examiner acceptor solution flow path 13b

Transfer efficiency, % = $\dfrac{\text{Accepter}, \mu M}{\text{Sample}, \mu M} \times 100$

PRETREATMENT DEVICE FOR DISSOLVED IONS ANALYSIS AND DISSOLVED ION ANALYSIS SYSTEM

CROSS-REFERENCE TO RELATED APPLICATION

The present application is based on the International Application No. PCT/JP2011/069567 which was filed on Aug. 30, 2011 and claims priority under 35 U.S.C. §119 from Japanese Patent Application No. 2010-268404 which was filed on Dec. 1, 2010.

TECHNICAL FIELD

The present invention relates to a pretreatment device for dissolved ions analysis and dissolved ion analysis system. More particularly, the present invention relates to a pretreatment device and a method thereof for separating and concentrating dissolved ions in a sample solution as a pretreatment for dissolved ion analysis, as well as to dissolved ion analysis system provided with the pretreatment device.

BACKGROUND ART

It is demanded in quality management in a production process, waste water treatment, environmental analysis, measurement of a biological sample, and the like that dissolved ions contained in a sample solution is measured.

The dissolved ions in the sample solution can be measured with an analysis apparatus such as an ion chromatograph; however, at least a removal of fine particles in the sample solution by filtering is needed. Further, in the case of a sample solution containing protein or lipid, there is a need to remove these. For example, for measurement of a slight amount of ions (perchlorate ion and the like) in cow milk, removal by adsorption of organic compounds with use of an alumina column or decomposition of organic substances by an ultraviolet light is needed in addition to removal of protein by centrifugation, so that several hours are required for analysis of one sample solution.

Also, in the case in which the dissolved ions to be measured that is contained in the sample solution is trace amount or the like, it is demanded that the dissolved ions to be measured is selectively extracted into an extraction liquid (typically, water) from the sample solution in order to improve the measurement precision.

As a method for pretreatment of such a sample solution, there is a method of extracting dissolved ions to be measured by concentration diffusion using a dialysis membrane (for example, see Non-patent Document 1: Journal of Chromatography A, 919(2001)59-65).

In this method, two flow channels are provided so as to intercalate a diffusion dialysis membrane therebetween, where a sample solution is supplied to one of the channels, and an acceptor solution (typically, water) is supplied to the other one of the channels. The dissolved ions contained in the sample solution are moved by concentration diffusion to the acceptor solution side via the diffusion dialysis membrane.

However, by the above pretreatment method, a long period of time is required for a diffusion when the dissolved analyte ion that is contained in the sample solution is low in concentration, thereby raising a problem of increased period of time for measurement.

SUMMARY OF THE INVENTION

Under such circumstances, an object of the present invention is to provide a pretreatment device for dissolved ions analysis, which enables the separation of dissolved ions to be analyzed from a sample solution in a short period of time and which is applicable to both a case in which the dissolved ions to be measured is a cation and a case in which the dissolved ions to be measured is an anion, as well as dissolved ion analysis system having the pretreatment device.

A pretreatment device for analysis of dissolved ions of the present invention includes a sample solution flow channel through which a sample solution containing dissolved analyte ions flows; an acceptor solution flow channel which is arranged adjacent to the sample solution flow channel so as to intercalate a dialysis membrane between the acceptor solution flow channel and the sample solution flow channel; a pair of electrodes which are so arranged as to intercalate the sample solution flow path and the acceptor solution flow channel therebetween; and a direct current power source which enables the generation of a predetermined potential difference between the electrodes.

According to this construction, the dissolved analyte ions in the sample solution that flows through the sample solution flow channel permeates through the dialysis membrane by being accelerated under an electric field between the two electrodes, so as to be taken out into the acceptor solution within the acceptor solution flow channel. For this reason, the dissolved analyte ions can be selectively taken out into the acceptor solution even from a sample solution containing a complex matrix. Further, since the dissolved analyte ions is accelerated by the electric field, the dissolved ions can be extracted into the acceptor solution flow channel in a short period of time even when the dissolved ions are low concentrations. Also, almost all of the dissolved analyte ions in the sample solution can be forcibly moved to the acceptor solution flow channel side by the electric field. For this reason, the dissolved analyte ions can be measured at a high precision in a short period of time by providing analyzing means for analyzing the acceptor solution at a stage posterior to the acceptor solution flow channel.

Also, depending on the analysis apparatus, there may be a case in which the measurement precision decreases when the dissolved analyte ions is too high in concentration. On the other hand, with the pretreatment device of the present invention, a sample solution in which the concentration of the dissolved analyte ions is high can be flowed out after being diluted by controlling the flow rate of the acceptor solution. For this reason, an acceptor solution containing the dissolved ions at a concentration suitable for the analysis apparatus can be obtained both in a case in which the dissolved ions concentration in the sample solution is a low concentration and in a case in which the dissolved ions concentration in the sample solution is a high concentration, so that a quick and high-precision measurement can be carried out.

The dissolved analyte ions are not particularly limited and may be, for example, an inorganic ion such as an alkaline metal ion, an alkaline earth metal ion, a halide ion, or an oxo acid ion, an organic ion such as an ion of carboxylic acid such as formic acid, acetic acid, or succinic acid, or the like.

The pretreatment device of the present invention is characterized in that a dialysis membrane is used as the ion transfer membrane. Here, in the present invention, the term "dialysis membrane" refers to a membrane which is electrically neutral and which can perform separation in accordance with the size of the molecule, so that a so-called cation exchange membrane or anion exchange membrane does not fall within the range of the dialysis membrane in the present invention.

By using such an electrically neutral dialysis membrane, the pretreatment device of the present invention has an advantage of being applicable to both a case in which the object of measurement is a cation and a case in which the object of measurement is an anion.

Here, when the object of measurement is a cation, it is sufficient that the electrode provided in the sample solution flow channel is made to be a positive electrode and the electrode provided on the acceptor solution flow channel side is made to be a negative electrode. When the object of measurement is an anion, it is sufficient that the electrode provided in the sample solution flow channel is made to be a negative electrode and the electrode provided on the acceptor solution flow channel side is made to be a positive electrode. In other words, in the pretreatment device of the present invention, each of a cation and an anion can be made to be an object of measurement by switching the electrode polarity.

The molecular weight cut off (MWCO) of the dialysis membrane is preferably 2000 to 15000, more preferably 3500 to 13000, and especially preferably 5000 to 10000. When the molecular weight cut off of the dialysis membrane is less than 2000, there is a problem in that the characteristics of extracting the dissolved ions are considerably deteriorated. When the molecular weight cut off of the dialysis membrane exceeds 15000, water serving as a solvent moves between the channels by pressure difference, thereby raising a fear that the ion concentration in the acceptor solution may fluctuate relative to the applied voltage.

When the molecular weight cut off of the dialysis membrane is within the above-described range, movement of the solvent between the channels by pressure difference hardly takes place, so that a more precise measurement can be made.

A material of the dialysis membrane may be, for example, cellulose, acrylonitrile, or the like. In particular, it is preferable that the dialysis membrane is a cellulose dialysis membrane because the cellulose dialysis membrane has a high hydrophilicity and can decrease adsorption of a hydrophobic substance to the membrane.

Examples of the cellulose constituting the cellulose dialysis membrane include a semi-synthesized cellulose obtained by denaturing a pure cellulose such as natural cellulose, regenerated cellulose, or cellulose acetate. The cellulose dialysis membrane may be a combination of two or more kinds of these celluloses for use.

The cellulose constituting the aforesaid cellulose dialysis membrane is preferably chemically modified with a modification compound because the characteristics of extracting the dissolved analyte ions species can be further more enhanced. Here, the term "chemical modification" means a modification obtained by reaction and bonding of a functional group in the cellulose with the modification compound. Substances whose permeation is inhibited by the modification compound can be suppressed from moving to the acceptor solution flow channel side, or the permeation characteristics of the ion to be extracted can be improved.

When the aforesaid modification compound is a compound having an electric charge, permeation of the ion species having an opposite electric charge can be suppressed. In other words, when the object of measurement is a cation, it is sufficient that the aforesaid modification compound is a compound having a negative electric charge. When the object of measurement is an anion, it is sufficient that the aforesaid modification compound is a compound having a positive electric charge.

Here, a functional group that the compound having an electric charge, which is introduced into the cellulose, has may be, for example, a functional group having a positive electric charge such as a quaternary amino group, a sulfonium group, or a vinylpyridine group; or a functional group having a negative electric charge such as a hydroxyl group, a sulfonic acid group, a phosphoric acid group, or a carboxyl group; however, the functional group is not limited to these.

In particular, since cellulose has a negative surface potential, anions tend to be less likely to permeate cellulose as compared with cations. For this reason, it is effective for permeation of anions to modify the cellulose with a compound having a functional group having a positive electric charge.

Also, in the case of an object of analysis, such as blood or cow milk, containing a biological component such as cells or protein, it is preferable that the aforesaid modification compound is a compound having a small interaction to the biological component. By modifying with such a compound, adsorption of the biological component onto the cellulose dialysis membrane can be suppressed.

A suitable specific example of the compound having a small interaction to the biological component may be 2-methacryloyloxyethylphospholycorine (MPC). Since MPC is the same polar group as the phosphorus lipid molecule which is a major component constituting the biological membrane, adsorption of protein or cells can be effectively evaded.

It is sufficient that the aforesaid modification compound is a compound having a moiety that is chemically or physically bonded to these functional groups and the cellulose membrane. Specifically, the modification compound may be acrylate or methacrylate to which the aforesaid functional group having an electric charge is bonded.

The cellulose can be chemically modified by bonding such a compound (monomer) to the cellulose by a method such as graft polymerization, the cerium ion method, or the electron beam irradiation method.

It is sufficient that the acceptor solution used in the pretreatment device for analysis of dissolved ions of the present invention is a solvent that does not contain the dissolved analyte ions. Specifically, the acceptor solution may be, for example, water, alcohol such as ethanol, or a mixture liquid of water-alcohol. Among these, water (suitably, purified water) is typically used.

Here, the pretreatment device for analysis of dissolved ions of the present invention has a structure such that a pair of electrodes are so arranged as to intercalate the aforesaid sample solution flow channel and the aforesaid acceptor solution flow channel therebetween. The pretreatment device may be a lamination type in which one of the electrodes, the aforesaid sample solution flow channel, the aforesaid acceptor solution flow channel, and the other one of the electrodes are stacked in this order. Alternatively, the pretreatment device may be a tubular type in which one electrode wire is passed through the center; the aforesaid sample solution flow channel and the aforesaid acceptor solution flow channel are arranged therearound; and the outermost wall is made to be the other electrode.

Also, in the pretreatment device for analysis of dissolved ions of the present invention, the aforesaid acceptor solution flow channel may be provided on both sides of the aforesaid sample solution flow channel so as to intercalate the aforesaid sample solution flow channel therebetween. By adopting such a construction, the cation and the anion can be simultaneously extracted to respectively different acceptor solution flow channels, so that both the cation and the anion can be simultaneously measured.

Further, it is preferable to provide an electrode separator on a front surface of an electrode provided in the aforesaid acceptor solution flow channel.

In the pretreatment device for analysis of dissolved ions of the present invention, a voltage is applied between the electrodes so as to promote the extraction of the dissolved analyte ions. When the applied voltage exceeds the electrolysis voltage of water serving as the solvent, oxygen is generated on the positive electrode side and hydrogen is generated on the negative electrode side by electrolysis of the water. When these gases are introduced together with the acceptor solution into the analyzing means of the posterior stage, there is a fear that these gases may be a cause of decrease in the analysis precision or troubles in the apparatus.

Here, by providing an electrode separator on the front surface of the electrode that is provided in the aforesaid acceptor solution flow channel, mingling of the gases generated due to the aforesaid electrolysis into the acceptor solution can be avoided, so that the analysis at the following stage is more precise and can be carried out easily.

As the electrode separator, a membrane through which the dissolved analyte ions and the gases generated due to the electrolysis do not permeate is used.

Specifically, when the electrode serving as an object is a negative electrode, an anion exchange membrane can be used, whereas when the electrode serving as an object is a positive electrode, a cation exchange membrane can be used. Also, a bipolar membrane obtained by bonding a cation exchange membrane and an anion exchange membrane with each other can be used in a direction considering the polarity of the electrode. Here, the term "direction considering the polarity of the electrode" refers to a direction such that the cation exchange surface is placed on the electrode side and the anion exchange surface is placed on the aforesaid acceptor solution flow channel side when the electrode is a negative electrode, whereas the anion exchange surface is placed on the electrode side and the cation exchange surface is placed on the aforesaid acceptor solution flow channel side when the electrode is a positive electrode. By adopting such a direction, the extracted ions can be prevented from being taken into the membrane, and the hydrogen ions and hydroxide ions generated at the boundary surface are efficiently supplied as counter ions.

Among these, it is preferable that the electrode separator is an ion exchange membrane. Together with the above-described generation of gases caused by the aforesaid electrolysis, there are an increase of hydrogen ions ($H^+$) in the neighboring the positive electrode and an increase of hydroxide ions ($OH^-$) in the neighboring the negative electrode. These ions are efficiently supplied as counter ions of the extracted ions by permeating through the membrane.

Also, dissolved ion analysis system of the present invention has the pretreatment device for analysis of dissolved ions according to the present invention described above, sample solution supplying means for supplying a sample solution to the sample solution flow channel of the pretreatment device, acceptor solution supplying means for supplying an acceptor solution to the acceptor solution flow channel of the pretreatment device, and analyzing means for analyzing the dissolved ions contained in the acceptor solution flowed out by passing through the acceptor solution flow channel of the pretreatment device.

In the pretreatment device of the present invention, because the dissolved analyte ions in the sample solution is forcibly moved to the acceptor solution flow channel, the dissolved analyte ions is concentrated to a high concentration in accordance with the flow rate ratio of the sample solution and the acceptor solution, so that a quick and high-precision analysis of the dissolved ions can be carried out.

Here, the sample solution supplying means and the acceptor solution supplying means are not particularly limited, so that a conventionally known liquid-supplying pump suitable for the solution flow rate can be used.

Also, the analyzing means at the stage posterior to the aforesaid pretreatment device is arbitrary and is suitably determined in accordance with the kind of the dissolved ions to be measured. Specifically, the analyzing means may be, for example, an ion chromatograph, an ICP emission spectrometer, an atomic absorption spectrometer, a mass spectrometer, or the like.

A pretreatment method for analysis of dissolved ions of the present invention is a method wherein, in a state in which a voltage is being applied to a pair of electrodes which are so arranged to intercalate a sample solution flow channel and an acceptor solution flow channel which is arranged adjacent to the sample solution flow channel so as to intercalate a dialysis membrane between the acceptor solution flow channel and the sample solution flow channel, an acceptor solution is allowed to flow through the acceptor solution flow channel while a sample solution containing dissolved ions to be measured is being allowed to flow through the sample solution flow channel, thereby the dissolved analyte ions is forcibly moved into the acceptor solution of the acceptor solution, so as to separate the dissolved analyte ions from the sample solution.

The pretreatment method of the present invention can be suitably carried out by using the above-described pretreatment device of the present invention.

The advantages obtained by the aforementioned present invention will be described hereinbelow.

The pretreatment device of the present invention enables the separation of dissolved analyte ions from a sample solution in a short period of time and is effective for a pretreatment in the analysis of an ion, such as the ion chromatography method, the ICP emission spectrometry method, the atomic absorption spectrometry method, and the mass spectrometry method. Also, the dissolved ion analysis system of the present invention provided with this pretreatment device enables quick and high-precision analysis of dissolved ions.

The above and other objects and advantageous features of the present invention will be made apparent from the following description made with reference to the accompanying drawings, in which reference characters designate the same or similar parts throughout the drawings.

DESCRIPTION OF THE PREFERRED EMBODIMENTS

Hereafter, suitable embodiments of the present invention will be described with reference to the drawings.

First Embodiment

Figure 1:
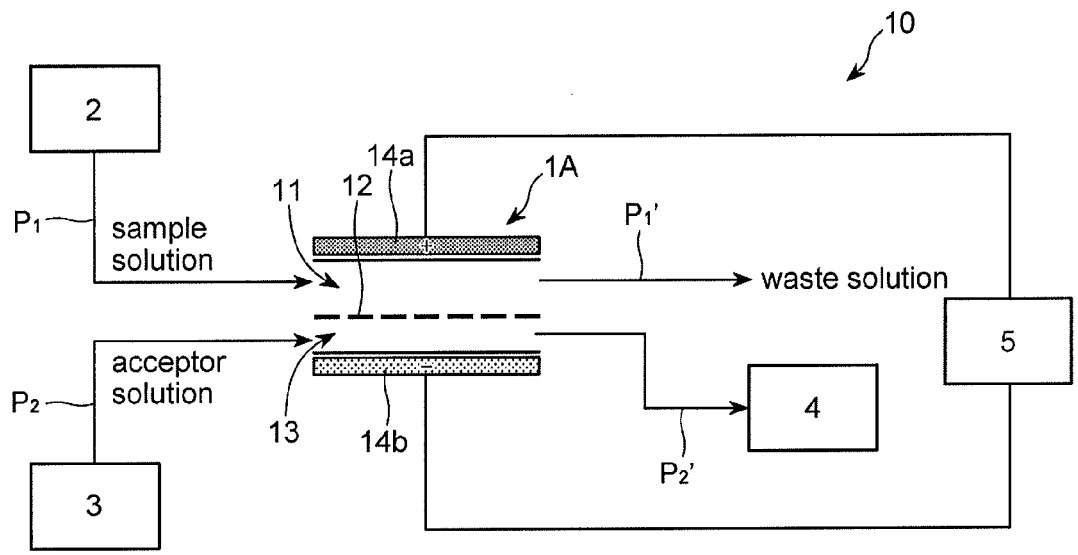
FIG. 1 is a conceptual view of dissolved ion analysis system of a first embodiment, provided with a pretreatment device 1A (flat plate lamination type).

FIG. 1 is a conceptual view of dissolved ion analysis system of a first embodiment of the present invention. Here, the dissolved ion analysis system of the first embodiment is a system used for measurement when dissolved ions to be measured are either cation or anion.

Referring to FIG. 1, dissolved ion analysis system 10 is mainly constructed with a pretreatment device 1A for analysis of dissolved ions, sample solution supplying means 2 for supplying a sample solution to the pretreatment device 1A, pure water supplying means 3 for supplying pure water, which is an acceptor solution, to the pretreatment device 1A, and analyzing means 4 for analyzing dissolved ions contained in the acceptor solution discharged by passing through the pretreatment device 1A.

The pretreatment device 1A has a laminated flat plate structure provided with a sample solution flow channel 11, a dialysis membrane 12, an acceptor solution flow channel 13, and a pair of electrodes 14a, 14b. Also, the pretreatment device 1A has a direct current power source 5 which enables the generation of a predetermined potential difference between the electrodes 14a, 14b.

In the pretreatment device 1A, a sample solution supplied from the sample solution supplying means 2 is supplied to the sample solution flow channel 11 via a liquid-transporting pipe $P_1$ and is discharged via a liquid-transporting pipe $P_1'$. Here, as the sample solution supplying means 2, a conventionally used liquid-transporting pump can be used.

On the other hand, the channel acceptor solution flow channel 13 is provided to be adjacent to the sample solution flow channel 11 so as to intercalate the dialysis membrane 12 extending along the flow channel direction between the acceptor solution flow channel 13 and the sample solution flow channel 11. Water supplied from the pure water supplying means 3 is supplied to the acceptor solution flow channel 13 via a liquid-transporting pipe $P_2$ and is thereafter discharged in a state of containing the dissolved ions to be measured, so as to be introduced to the analyzing means 4 of the posterior stage via a liquid-transporting pipe $P_2'$. Here, as the pure water supplying means 3, a conventionally used liquid-flow pump can be used. Also, as the analyzing means 4, an ion chromatograph, an ICP emission spectrometer, an atomic absorption spectrometer, a mass spectrometer, or the like can be suitably used.

The dialysis membrane 12 is an electrically neutral membrane through which the dissolved ions can permeate and fine particles or macromolecules such as protein contained in the sample solution do not permeate. Specifically, a dialysis membrane made of a hydrophobic substance (solid or liquid) such as lipids or organic solvents is used, and a cellulose membrane is suitable.

Here, as the cellulose membrane, a cellulose membrane having a MWCO of 2000 to 15000, suitably a MWCO of 3500 to 13000, and especially suitably a MWCO of 5000 to 10000, is suitably used.

Also, for the purpose of suppressing the membrane permeation other than the object of measurement, a cellulose dialysis membrane chemically modified with a modification compound can be used as well.

Electrodes 14a, 14b, having a flat plate shape, are arranged on both sides so as to intercalate the sample solution flow channel 11 and the acceptor solution flow channel 13 therebetween. Further, the pretreatment device 1A has a direct current power source 5 that can apply a predetermined voltage to the electrodes 14a, 14b.

Figure 2:
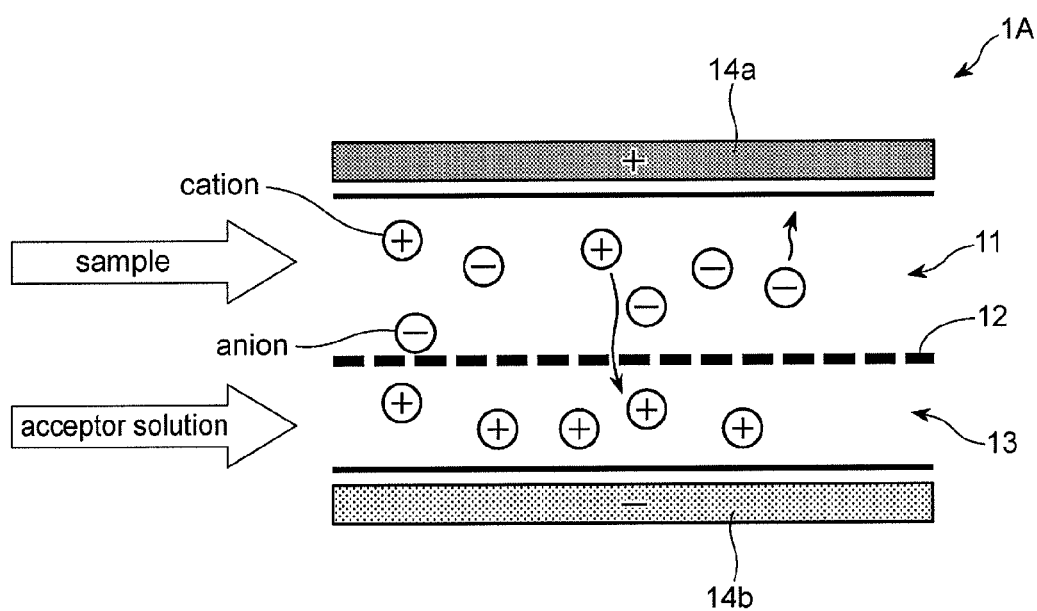
FIG. 2 is a descriptive view of dissolved ion separation by the pretreatment device 1A (flat plate lamination type) of the present invention.

Hereafter, with reference to FIG. 2, a method of operation in the case in which the object of measurement is a cation in the pretreatment device 1A will be described. Here, when the object of measurement is an anion, the electrode polarities of the electrodes 14a, 14b may be reversed in the following description.

First, the direct current power source 5 is connected so that the electrode 14a is a positive electrode and the electrode 14b is a negative electrode. Subsequently, a sample solution containing a cation to be measured is supplied to the sample solution flow channel 11 at a predetermined flow rate, and water serving as an acceptor solution is supplied to the acceptor solution flow channel 13 at a predetermined flow rate, thereafter a predetermined voltage is applied between the electrodes 14a, 14b.

In the sample solution flowing through the sample solution flow channel 11, there exist an anion, neutral molecules, and fine particles in addition to the cation to be measured. However, by potential gradient formed between the electrodes 14a, 14b, the cation to be measured is attracted to the electrode 14b (negative electrode) and moves to the acceptor solution flow channel 13 after permeating through the dialysis membrane 12.

On the other hand, the anion which is not an object of measurement is attracted to the electrode 14a (positive electrode) side and remains within the sample solution flow channel 11 to be exhausted to the outside from the sample solution flow channel 11.

As a result, only the cation to be measured is supplied to the analyzing means 4 of the posterior stage so as to be measured after passing through the acceptor solution flow channel 13.

Here, in the construction of the pretreatment device 1A, the respective thicknesses of the sample solution flow channel 11 and the acceptor solution flow channel 13 are determined by considering the liquid-transporting amounts of the solution to be used and the acceptor solution, and the potential gradient between the electrodes 14a, 14b. In particular, when the distance between the electrodes 14a, 14b is too large, a needed potential gradient is not obtained, thereby raising a fear that the effect of the present invention, that is, movement of the dissolved ions to be measured to the acceptor solution flow channel 13 by voltage application, may not be obtained. Therefore, the distance between the electrodes 14a, 14b is preferably small. Suitably, the thickness of each solution layer is 100 to 500 µm.

Here, the applied voltage is suitably determined also depending on various conditions such as the kind of the dissolved ions to be measured, the structure of the pretreatment device 1A, the selection of the dialysis membrane 12, and the flow rates of the sample solution and the acceptor solution; however, the applied voltage is typically about 1.5 V to 40 V.

Figure 3:
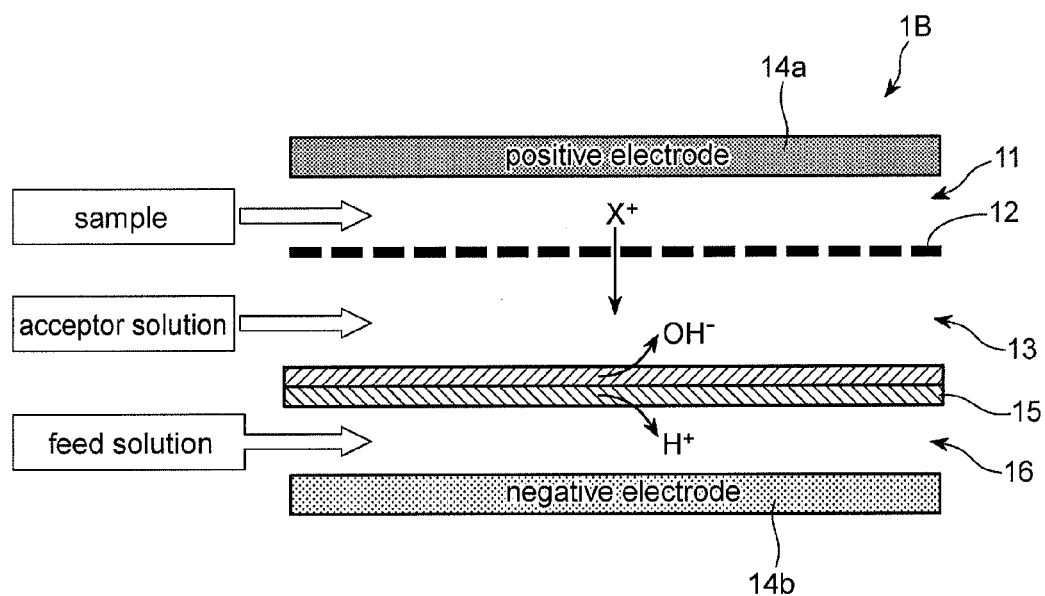
FIG. 3 is a conceptual cross-sectional view of a pretreatment device 1B (flat plate lamination type) of the present invention.

Here, in the construction of the pretreatment device 1A described above, the electrode 14b has a structure of being in direct contact with the acceptor solution of the acceptor solution flow channel 13. However, an electrode separator 15 may be provided on a front surface of the electrode 14b on the acceptor solution flow channel 13 side as in the pretreatment device 1B shown in FIG. 3. By providing the electrode separator 15, mingling of the gases generated due to the aforesaid electrolysis into the acceptor solution can be avoided, so that the analysis at the posterior stage is more precise, and also the apparatus troubles can be avoided.

As the electrode separator 15, a membrane through which ions selectively permeate and air bubbles of the gas (positive electrode side: oxygen, negative electrode side: hydrogen) generated due to electrolysis of water by application of electric potential between the electrodes 14a, 14b do not permeate is used. As the electrode diaphragm 15, specifically, a bipolar membrane obtained by bonding a cation exchange membrane and an anion exchange membrane with each other can be used. However, since the bipolar membrane has a large film thickness to increase the membrane resistance, an anion exchange membrane is suitably used in the case in which the object of measurement is a cation, and a cation exchange membrane is suitably used in the case in which the object of measurement is an anion.

Here, a feed solution is allowed to flow through a feed solution supplying flow channel 16 between the electrode 14b and the electrode separator 15 by feed solution supplying means, thereby the gas generated at the electrode can be removed. As the feed solution, pure water or ion exchange water is typically used; however, the feed solution is not limited to this.

Here, the pretreatment device 1A has a structure such that constituent parts respectively having a flat plate shape are laminated and the gaps between these are sealed. In other words, the pretreatment device 1A is of a lamination type in which the electrode 14a, the sample solution flow channel 11, the dialysis membrane 12, the acceptor solution flow channel 13, and the electrode 14b are laminated in this order.

Figure 4:
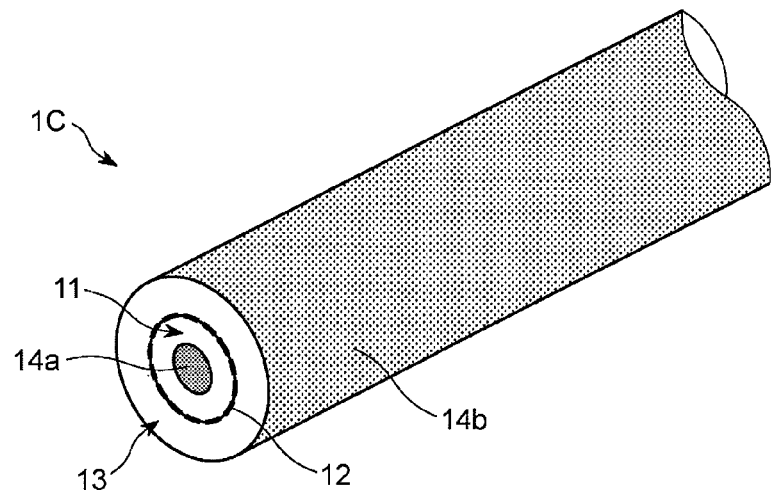
FIG. 4 is a conceptual cross-sectional view of a pretreatment device 1C (tubular type) of the present invention.

On the other hand, the pretreatment device may be of a tubular type in which an electrode 14a having a wire shape is located at the center; the sample solution flow channel 11, the dialysis membrane 12, and the acceptor solution flow channel 13 described above are provided therearound; and the outermost wall is made to be the electrode 14b, as in the pretreatment device 1C shown in FIG. 4.

There is a limit in designing the pretreatment device 1C of a tubular type; however, there is an advantage in that the distance between the two electrodes can be easily made small so as to increase the electric potential gradient. Also, in the pretreatment device 1A of a lamination type, liquid leakage is liable to occur due to a problem in sealing each layer, whereas in the pretreatment device 1C, sealing is unnecessary, thereby providing an advantage in that the liquid leakage hardly occurs.

Second Embodiment

Dissolved ion analysis system provided with a pretreatment device for analysis of dissolved ions according to the second embodiment of the present invention will be described with reference to the drawings. The dissolved ion analysis system according to the second embodiment is a system in which a cation and an anion can be respectively simultaneously measured as objects of measurement.

Here, in the second embodiment, constituent elements having the same construction as in the first embodiment may be denoted with the same reference symbols, and the description thereof may be omitted.

Figure 5:
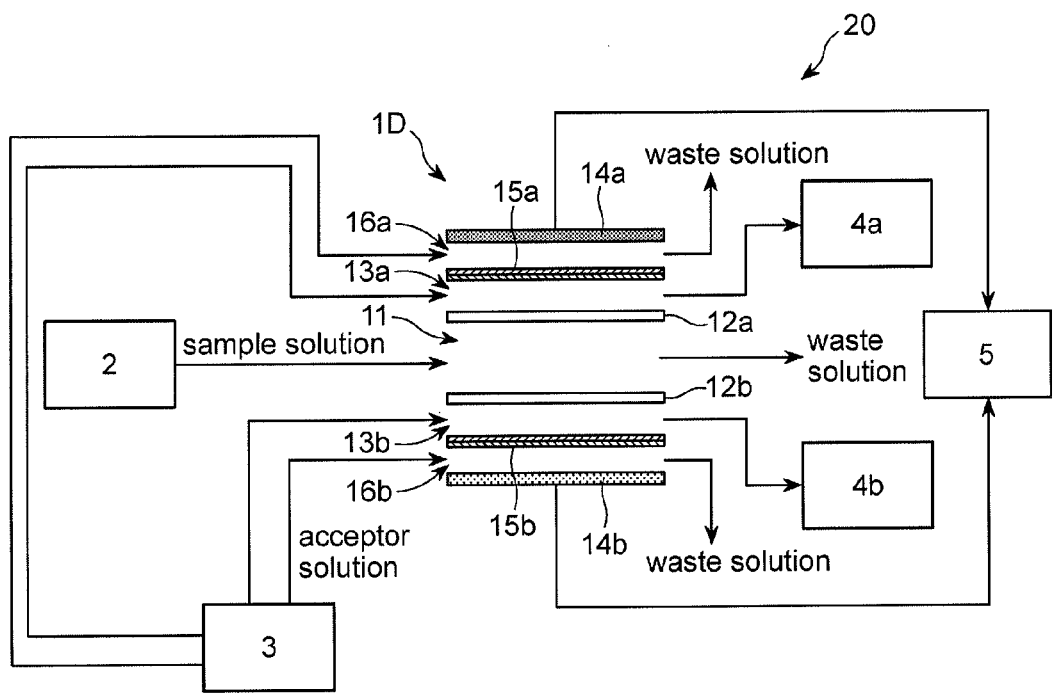
FIG. 5 is a conceptual view of dissolved ion analysis system of a second embodiment, provided with a pretreatment device 1D (flat plate lamination type) of the present invention.

FIG. 5 is a conceptual view of dissolved ion analysis system according to the second embodiment of the present invention.

Referring to FIG. 5, the dissolved ion analysis system 20 is mainly constructed with a pretreatment device 1D for analysis of dissolved ions, sample solution supplying means 2 for supplying a sample solution to the pretreatment device 1D, pure water supplying means 3 for supplying pure water, which is an acceptor solution and a feed solution, to the pretreatment device 1D, and analyzing means 4a, 4b for analyzing dissolved ions contained in the acceptor solution obtained by passing through the pretreatment device 1D.

The pretreatment device 1D has a laminated flat plate structure provided with an electrode 14a, a feed solution supplying flow channel 16a, an electrode separator 15a, an acceptor solution flow channel 13a, a dialysis membrane 12a, a sample solution flow channel 11, a dialysis membrane 12b, an acceptor solution flow channel 13b, an electrode separator 15b, a feed solution supplying flow channel 16b, and an electrode 14b. Also, the pretreatment device 1D has a direct current power source 5 which enables the generation of a predetermined potential difference between the electrodes 14a, 14b.

Here, the pretreatment device 1D is characterized by having two acceptor solution flow channels 13a, 13b so as to intercalate the sample solution flow channel 11 therebetween. Because of having such a construction, the cation and the anion can be extracted to respectively different acceptor solution flow channel 13a, 13b, thereby enabling simultaneous measurement of both the cation and the anion.

In the pretreatment device 1D having the aforementioned construction, the electrode 14a is a positive electrode; the electrode 14b is a negative electrode; the electrode separator 15a is a cation exchange membrane; and the electrode separator 15b is an anion exchange membrane.

The feed solution flow channel 16a (16b) is a flow channel provided between the electrode 14a (14b) and the electrode separator 15a (15b). By allowing the feed solution to flow through this flow channel, H⁺, OH⁻, hydrogen gas, and oxygen gas generated by electrolysis caused by voltage application between the electrodes 14a, 14b can be forcibly let to flow and washed away.

Figure 6:
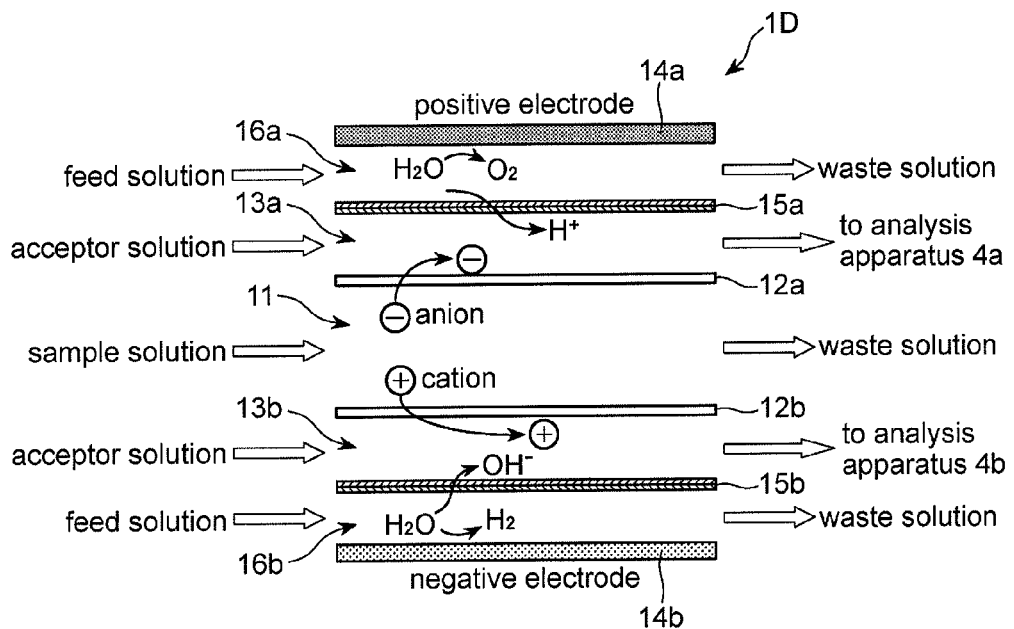
FIG. 6 is a descriptive view of dissolved ion separation by the pretreatment device 1D (flat plate lamination type) of the present invention.

Hereafter, with reference to FIG. 6, a method of operating the pretreatment device 1D will be described.

First, the direct current power source 5 is connected so that the electrode 14a is a positive electrode and the electrode 14b is a negative electrode. Subsequently, a sample solution containing a cation to be measured is supplied to the sample solution flow channel 11 at a predetermined flow rate, and pure water is supplied to the acceptor solution flow channels 13a, 13b and the feed solution supplying flow channels 16a, 16b. Further, an electric potential gradient is formed between the electrodes 14a, 14b by applying a predetermined voltage between the electrodes 14a, 14b.

The anion contained in the sample solution flowing through the sample solution flow channel 11 is attracted to the electrode 14a (positive electrode) and moves to the acceptor solution flow channel 13a by permeating through the dialysis membrane 12a. On the other hand, the cation is attracted to the electrode 14b (negative electrode) and moves to the acceptor solution flow channel 13b by permeating through the dialysis membrane 12b.

Here, the extraction characteristics are improved when the dialysis membrane 12a is chemically modified by a compound having a negative electric charge and the dialysis membrane 12b is chemically modified by a compound having a positive electric charge so as to have an electric charge opposite to that of the ion to be measured. Here, fine particles and macromolecules such as protein cannot permeate through the dialysis membranes 12a, 12b, and are discharged to the outside as they are. Also, non-ionic organic compounds are flowed out to the outside as they are, because the non-ionic organic compounds are not affected by the electric field and hardly permeate through the membranes. In order to enhance the removal performance, the dialysis membrane 12a and the dialysis membranes 12b may be modified with a compound having an ion exchange property.

As a result, only the anion to be measured is extracted to the acceptor solution flow channel 13a, and only the cation to be measured is extracted to the acceptor solution flow channel 13b, so as to be supplied to the analyzing means 4a, 4b of the following stage and respectively measured independently.

Here, as the analyzing means 4a, 4b, an ion chromatograph, an ICP emission spectrometer, an atomic absorption spectrometer, a mass spectrometer, or the like can be suitably used. However, in the present embodiment, since only the anion is an object of measurement in the analyzing means 4a and only the cation is an object of measurement in the analyzing means 4b, an ion chromatograph having a respectively suitable column can be a suitable example of the analyzing means.

As shown above, the embodiments of the present invention have been described; however, the present invention is not limited to the above-described embodiments.

EXAMPLES

Hereafter, the present invention will be described in more detail by way of Examples; however, the present invention is not limited to the following Examples unless the gist thereof is changed.

Example 1

Double Tubular Type Pretreatment Device (Two Solution Layer Type)

By using dissolved ion analysis system 10 that accords to the construction shown in FIG. 1, an experiment of extracting dissolved ions contained in a sample solution was conducted. As the pretreatment device, a pretreatment device 1C of a double tubular type was used in place of the pretreatment device 1A shown in FIG. 1.

The construction of the pretreatment device 1C in the dissolved ion analysis system 10 that was actually put to use is as follows. Here, a peristaltic pump manufactured by Rainin Co., Ltd. was used as the sample solution supplying means 2 and the pure water supplying means 3, and an ion chromatograph (Nippon Dionex K.K., ICS-1100, separation column: CS12A) was used as the analyzing means 4.

[Pretreatment Device 1C]

Electrode 14a (positive electrode): platinum wire (DIA 100 μm)

Dialysis membrane 12: regenerated cellulose micro dialysis tube (MWCO 13000) manufactured by Spectrum-Laboratories Co., Ltd.

OD 216 μm, ID 200 μm, effective length 120 mm

Electrode 14b (negative electrode): stainless pipe (effective length 120 mm)

OD 710 μm, ID 400 μm, effective length 120 mm

Here, in the pretreatment device 1C, two solution layers are constructed by passing a platinum wire through the inside of an extremely thin dialysis membrane tube and jacketing the outside with a stainless pipe. In the above construction, the length of the sample solution flow channel 11 is 50 μm; the length of the acceptor solution flow channel 13 is 92 μm; the effective volume of the sample solution flow channel 11 is 2.9 μL; and the effective volume of the acceptor solution flow channel 13 is 11 μL.

(Evaluation 1)

As the sample solution, a cation mixed solution containing three kinds of cations (Li⁻, K⁺, Ca²⁺) respectively at 50 μM was used.

Figure 7:
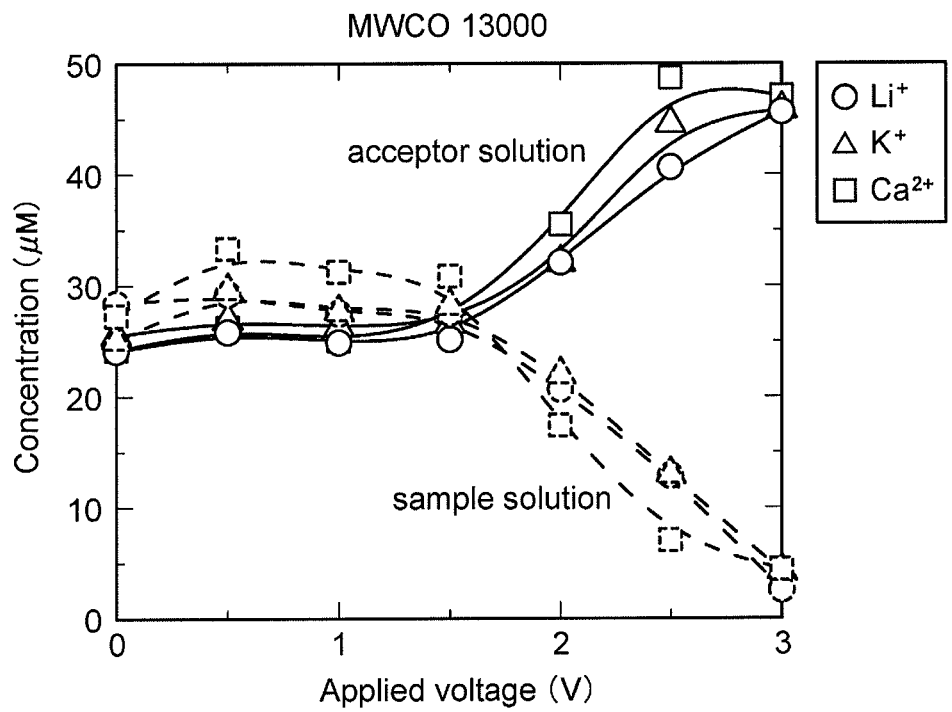
FIG. 7 is a view showing a relationship between an applied voltage and an effect of extracting dissolved ions in Example 1 (pretreatment device 1C (tubular type)).

The cation mixed solution was allowed to flow through the sample solution flow channel 11 under conditions with a flow rate of 100 μL/min, and pure water was allowed to flow through the acceptor solution flow channel 13 under conditions with a flow rate of 100 μL/min. In this state, a voltage was applied between the electrodes 14a, 14b from the direct current power source 5. The introduced sample solution and extraction solution were captured respectively at exits of the device and were quantitated with an ion chromatograph to evaluate the characteristics of the migration membrane extraction. FIG. 7 shows a relationship between the applied voltage and the effect of extracting the dissolved ions in the pretreatment device 1C (tubular type).

With respect to the concentration of the cations (Li⁺, K⁺, Ca²⁺) in the extract solution, the concentration in the acceptor solution sharply rose at a voltage of 1.5 V or more, and 95% or more of the ions in the sample solution were taken out into the extraction water at around 3 V. The applied voltage of 1.5 V in the double tubular type corresponds to 120 V/cm in terms of potential gradient, and a high potential gradient that competes with electrophoresis promotes the movement of the ion and the membrane permeation. Also, it seems that, at around 1.5 V and onwards, the hydroxide ion (OH⁻) generated on the electrode surface by electrolysis of water functions as a counter ion of the extracted cation.

Example 2

Flat Plate Lamination Type Pretreatment Device (Three Solution Layers)

By using dissolved ion analysis system 10 that accords to the construction shown in FIG. 1, an experiment of extracting dissolved ions contained in a sample solution was conducted. As the pretreatment device, a pretreatment device 1B of a flat plate lamination type (three solution layers) was used in place of the pretreatment device 1A shown in FIG. 1.

The construction of the pretreatment device 1B in the dissolved ion analysis system 10 that was actually put to use is as follows. Here, as the sample solution supplying means 2, the pure water supplying means 3, and the analyzing means 4 besides that, the same apparatuses as those in the Example 1 were used, and a peristaltic pump was used for solution transportation to the feed solution supplying flow channel 16.

[Pretreatment Device 1B]

Electrode 14a (positive electrode): platinum plated mesh
Dialysis membrane 12: regenerated cellulose membrane (manufactured by
Spectrum-Laboratories Co., Ltd., Type: 129020, thickness: 18 μm)
Electrode separator 15: manufactured by ASTOM Corporation, NEOCEPTOR (registered trademark) BP-1E, thickness 220 μm (bipolar membrane)
Electrode 14b (negative electrode): platinum plated mesh
The sizes of the sample solution flow channel 11, the acceptor solution flow channel 13, and the feed solution supplying flow channel 16 in the pretreatment devices 1B having the above-described construction are as follows.
Sample solution flow channel 11: width 5 mm, length 120 mm, thickness 127 μm
Acceptor solution flow channel 13: width 5 mm, length 120 mm, thickness 127 μm
Feed solution supplying flow channel 16: width 5 mm, length 120 mm, thickness 127 μm
Here, for the dialysis membrane 12, five kinds of membranes with a molecular weight cut off (MWCO) of 3500, 5000, 8000, 15000, and 25000 were used.

Also, for comparison, a pretreatment device in which the following membrane was used as an ion permeation membrane that replaces the regenerated cellulose membrane was fabricated.

Cation exchange membrane: (SELEMION (registered trademark) CMV, manufactured by Asahi Glass Co., Ltd., thickness: 130 μm, 0.094 meq/channel)

(Evaluation 2-1)

Pretreatment devices 1B in which a regenerated cellulose membrane having an MWCO of 8000 was used as the dialysis membrane 12 and in which the above-described cation exchange membrane was used as a dialysis membrane 12' for comparison were respectively fabricated.

As the sample solution, a cation mixed solution containing three kinds of cations ($Li^-$, $K^+$, $Ca^{2+}$) respectively at 50 μM was used.

The cation mixed solution was allowed to flow through the sample solution flow channel 11 under conditions with a flow rate of 100 μL/min, and pure water was allowed to flow through the acceptor solution flow channel 13 and the feed solution flow channel 16 under conditions with flow rates of 100 μL/min and 100 μL/min, respectively. In this state, a voltage was applied between the electrodes 14a, 14b from the direct current power source 5. The introduced sample solution and acceptor solution were captured respectively at exits of the device and were quantitated with an ion chromatograph to evaluate the characteristics of the migration membrane extraction.

Figure 8A:
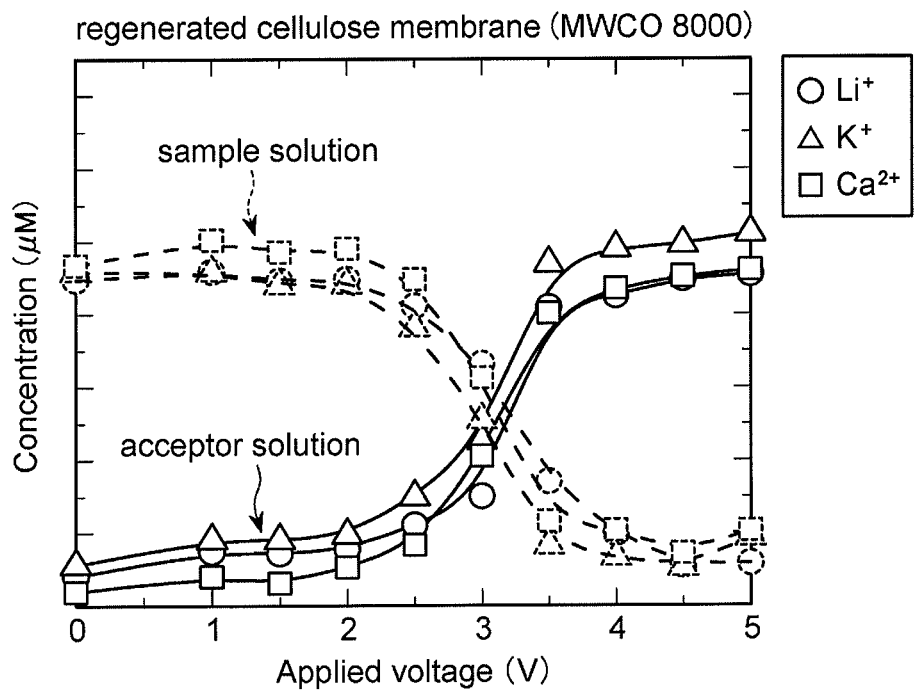
FIG. 8 is a view showing a relationship between an applied voltage and an effect of extracting dissolved ions when a dialysis membrane (ion permeation membrane) is made of (A) regenerated cellulose membrane or (B) cation exchange membrane in Example 2 (pretreatment device 1B (flat plate lamination type)).
Figure 8B:
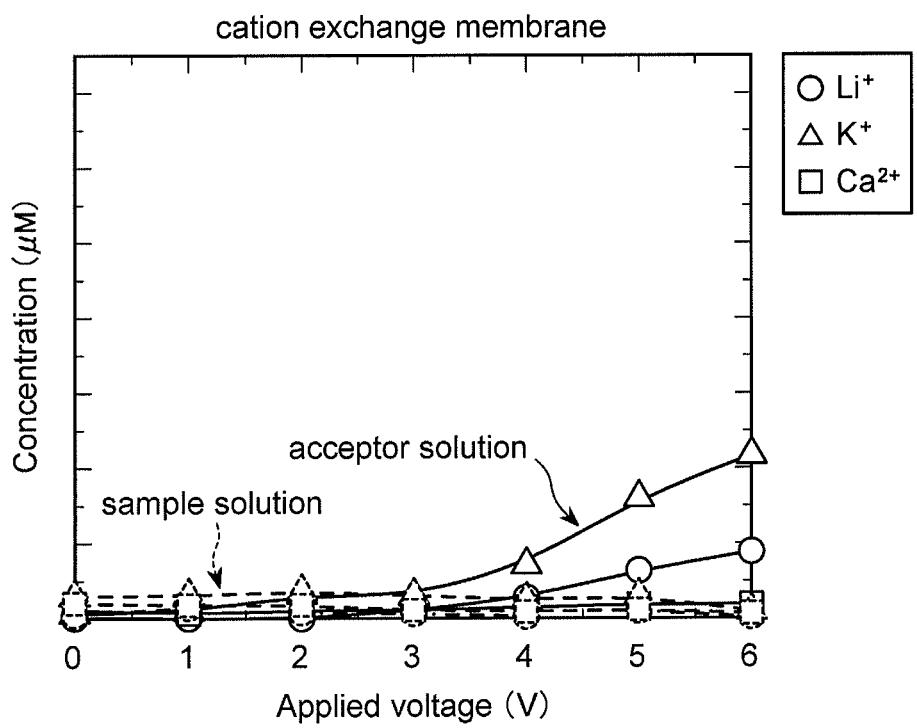
Figure 9A:
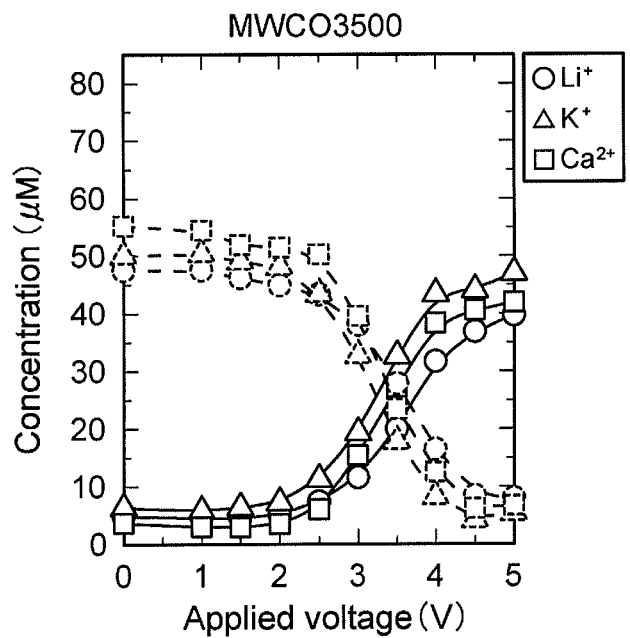
FIG. 9 is a view showing a relationship between an applied voltage and an effect of extracting dissolved ions when regenerated cellulose membranes having different molecular weight cut offs (MWCO) are used as a dialysis membrane in Example 2 (pretreatment device 1B (flat plate lamination type)).
Figure 9B:
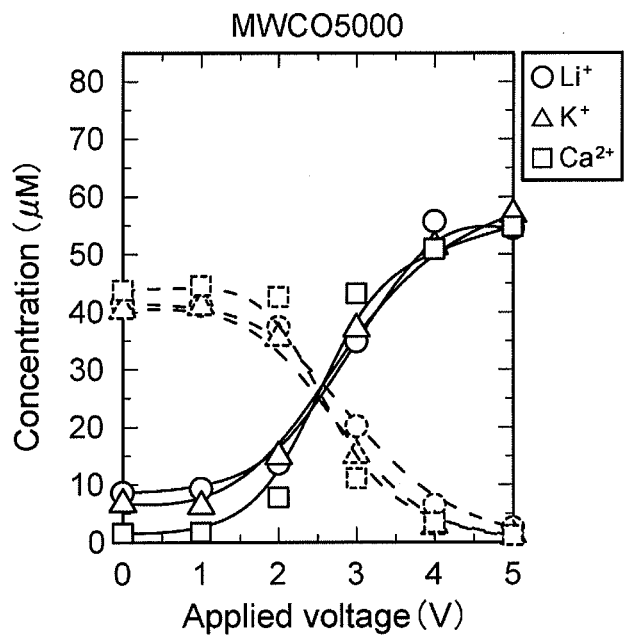
Figure 9C:
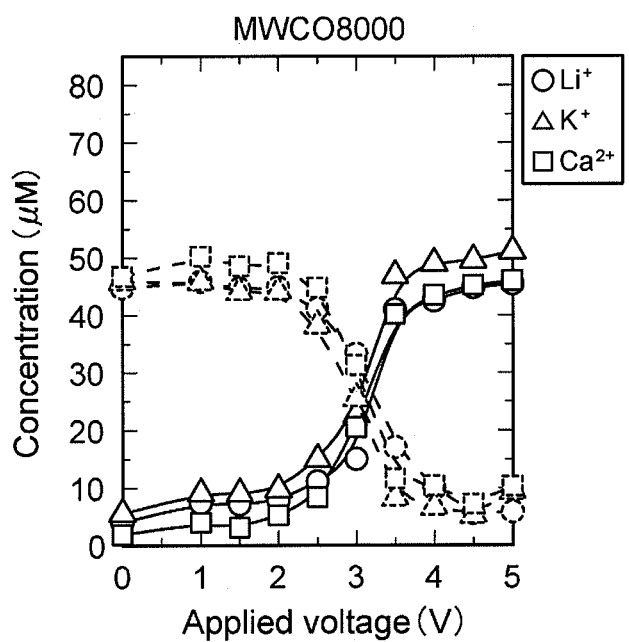
Figure 9D:
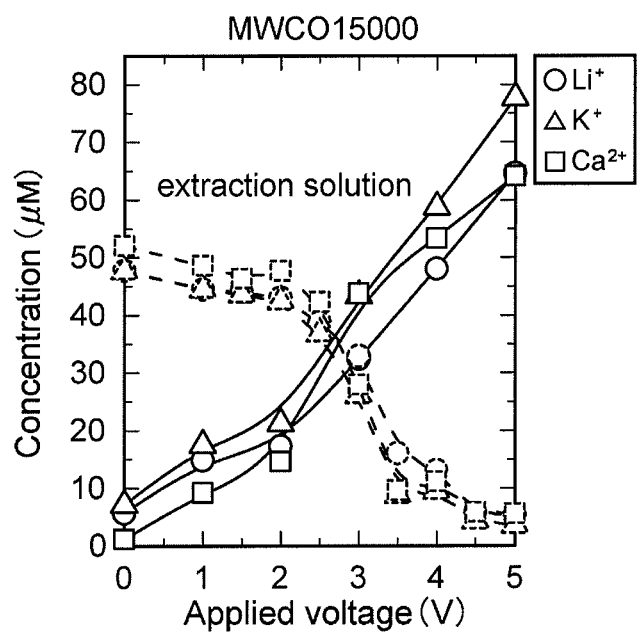
Figure 9E:
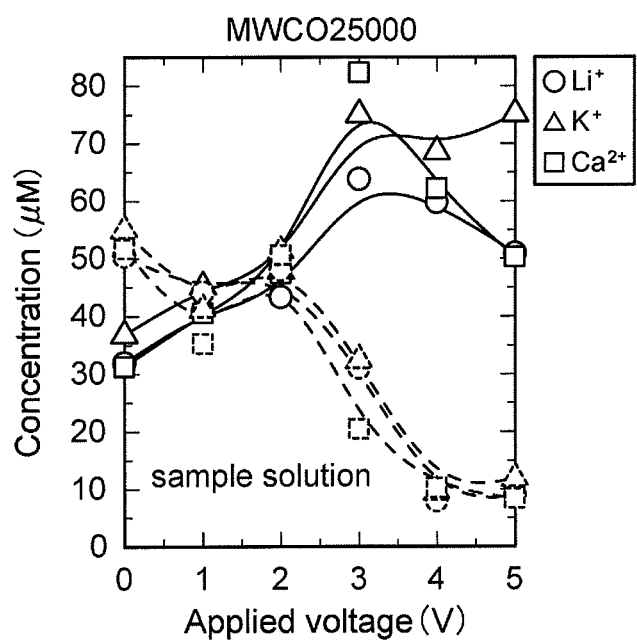

FIGS. 8(A) and 8(B) show a relationship between the applied voltage and the effect of extracting the dissolved ions when the respective ion permeation membranes were used.

As shown in FIG. 8(A), when a regenerated cellulose membrane (dialysis membrane, MWCO 8000) was used as the ion permeation membrane, the cation concentration in the acceptor solution increased in accordance with a rise in the applied electric potential. The cation mixed solution of 50 μM could be extracted at an applied voltage of about 4 V.

Also, it has been confirmed that the movement of gases to the acceptor solution flow channel 13 can be suppressed by isolating the electrode 14b with use of the electrode separator 15 which is a bipolar membrane. Also, by the bipolar membrane, the electric current value increased exponentially in accordance with an increase in the applied voltage. In accordance with an increase in the electric current, the cation concentration in the extraction solution also increased. At an electric potential of 4 V or more, 95% or more of the ions could be extracted from the 50 μM cation mixed solution.

Also, as shown in FIG. 8(B), when a cation exchange membrane (SELEMION (registered trademark) CMV) was used, the introduced cations could not be taken out into the extraction water though the introduced cations were all removed from the sample solution flow channel 11. It seems that this is because the cations to be measured were trapped by the cation exchange membrane.

In this manner, it has been found out that, in the pretreatment device of the present invention, the regenerated cellulose membrane which is a dialysis membrane is suitable.

(Evaluation 2-2)

FIG. 9 shows a relationship between the applied voltage and the effect of extracting the dissolved ions when five kinds of regenerated cellulose membranes having different molecular weight cut offs (MWCO) were used for the dialysis membrane 12.

From FIG. 9, it is understood that, with the regenerated cellulose membrane having a molecular weight cut off (MWCO) of 25000, the ion concentration varies though concentration of the ions in the acceptor solution could be carried out.

On the other hand, it is understood that, with the regenerated cellulose membrane having a molecular weight cut off (MWCO) of 15000, the variation in the ion concentration disappears and that, with the regenerated cellulose membranes having a molecular weight cut off (MWCO) of 8000, 5000, and 3500, the correlation of the ion concentration between the sample solution and the acceptor solution is high.

Example 3

Flat Plate Lamination Type Pretreatment Device (Five Solution Layers)

By using dissolved ion analysis system 20 that accords to the construction shown in FIG. 5, an experiment of extracting dissolved ions contained in a sample solution was conducted.

The construction of the pretreatment device 1D of a flat plate lamination type (five solution layers) in the dissolved ion analysis system 20 that was actually put to use is as follows. Here, as the sample solution supplying means 2, the pure water supplying means 3, the feed solution supplying flow channel 16, and the analyzing means 4a, 4b besides that, the same apparatuses as those in the Examples 1, 2 were used.

[Pretreatment Device 1D]

Electrode 14a (positive electrode): platinum plated mesh
Dialysis membrane 12a, 12b: regenerated cellulose membrane (manufactured by Spectrum-Laboratories Co., Ltd., Type: 129020, MWCO: 8000, thickness: 18 μm)
Electrode diaphragm 15a: cation exchange membrane (SELEMION (registered trademark) CMV manufactured by AGC Engineering Co., Ltd., thickness 130 μm)

Electrode diaphragm 15b: anion exchange membrane (SELEMION (registered trademark) AMV manufactured by AGC Engineering Co., Ltd., thickness 130 μm)

Electrode 14b (negative electrode): platinum plated mesh

The sizes of the sample solution flow channel 11, the acceptor solution flow channel 13, and the feed solution supplying flow channel 16 in the pretreatment devices 1D having the above-described construction are as follows.

Sample solution flow channel 11: width 5 mm, length 40 mm, thickness 127 μm Acceptor solution flow channel 13a, 13b: width 5 mm, length 40 mm, thickness 127 μm Feed solution supplying flow channel 16a, 16b: width 5 mm, length 40 mm, thickness 127 μm (Evaluation 3-1)

As the sample solution, a cation-anion mixed solution containing five kinds of cations ($Li^+$, $K^-$, $NH_4^+$, $Ca^{2+}$, $Mg^{2-}$) and four kinds of anions ($Br^-$, $NO_3^-$, $SO_4^-$, methanesulfonic acid (MSA)) respectively at 100 μM was used.

The cation mixed solution was allowed to flow through the sample solution flow channel 11 under conditions with a flow rate of 100 μL/min, and pure water was allowed to flow through the acceptor solution flow channel 13a, 13b and the feed solution supplying flow channels 16a, 16b under conditions with flow rates of 100 μL/min 100 μL/min, respectively. In this state, a voltage was applied between the electrodes 14a, 14b from the direct current power source 5. The introduced sample solution and extraction solution were captured respectively at exits of the device and were quantitated with an ion chromatograph to evaluate the characteristics of the migration membrane extraction.

Figure 10A:
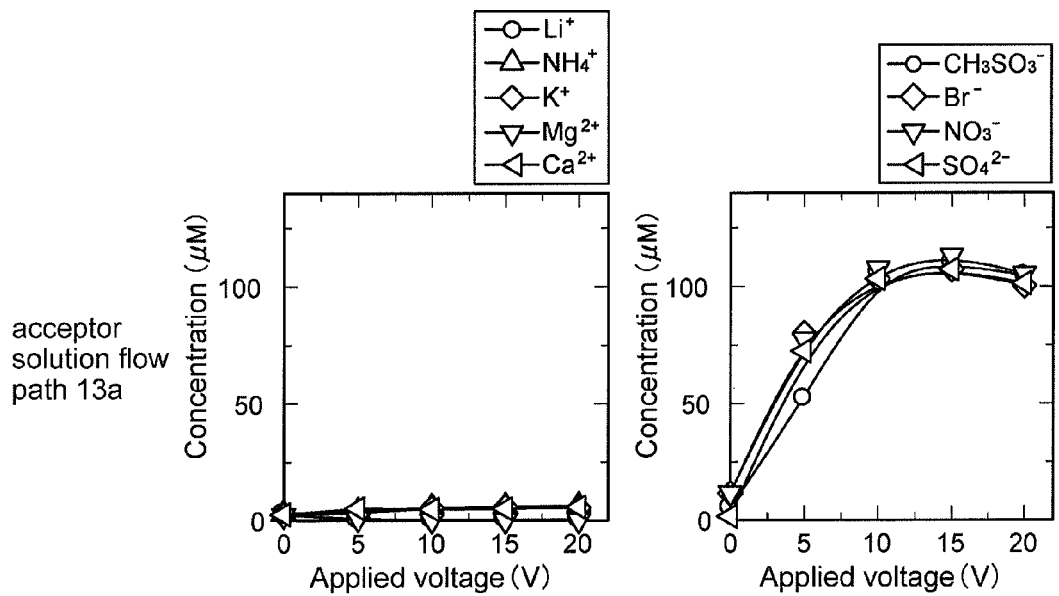
FIG. 10 is a view showing a result of evaluating cation and anion concentrations in the acceptor solution and the sample solution (waste solution) obtained from the pretreatment device 1D in Example 3 (pretreatment device 1D (flat plate lamination type)).
Figure 10B:
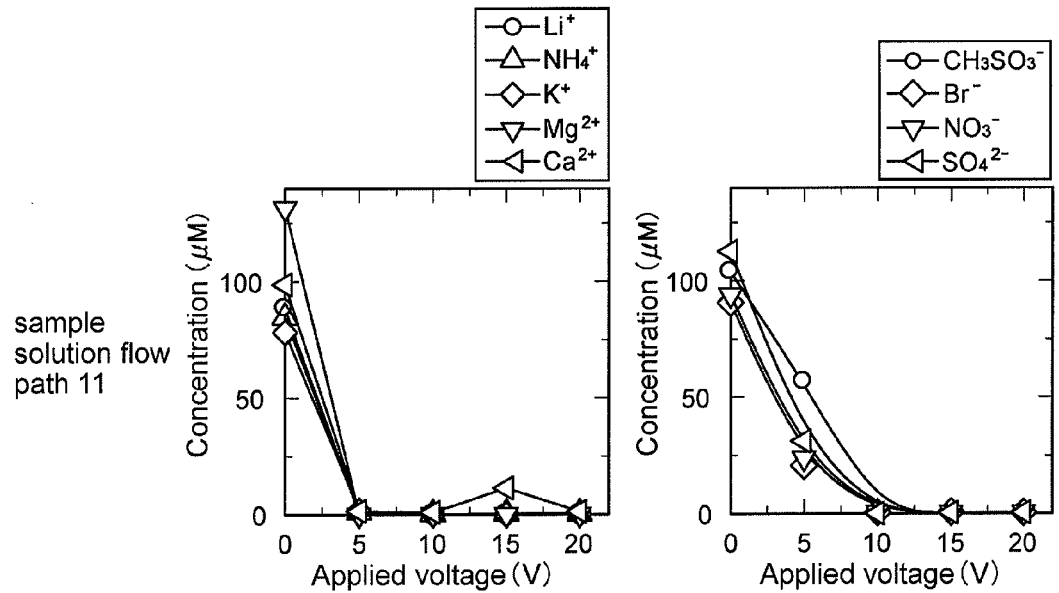
Figure 10C:
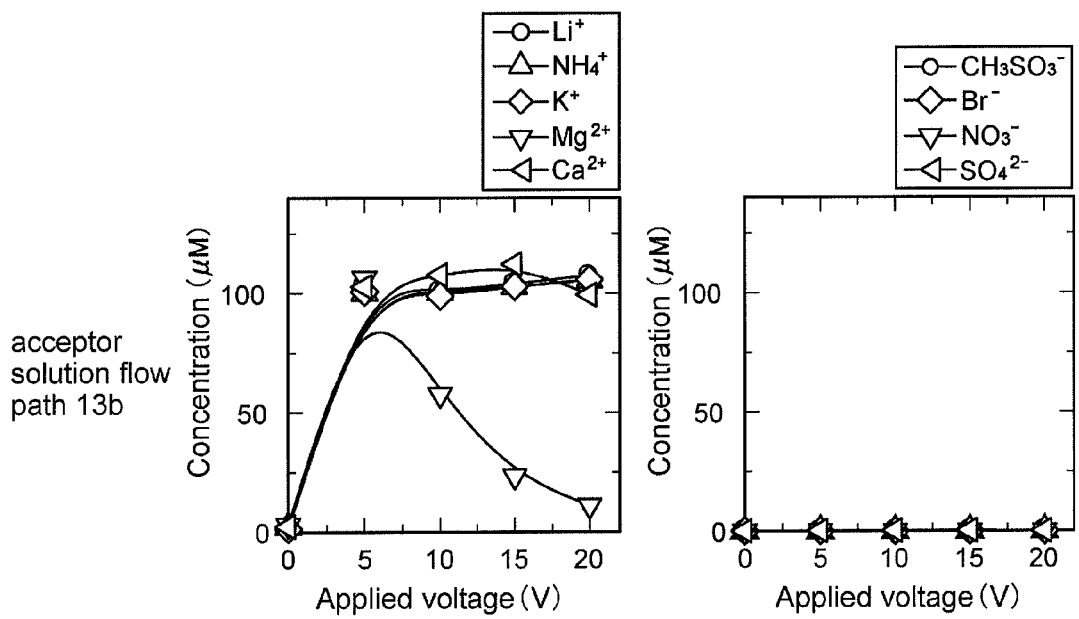

FIG. 10 shows a result of evaluation of the cation and anion concentrations in the acceptor solution discharged from the acceptor solution flow channels 13a, 13b and in the sample solution (waste liquid) discharged from the sample solution flow channel 11.

From FIG. 10, it is understood that both the cations and the anions are removed from the sample solution at an applied voltage of about 5 to 10 V. Further, the cations selectively move into the extraction water of the acceptor solution flow channel 13b, and the anions selectively move into the extraction water of the acceptor solution flow channel 13a.

Here, in the above-described 100 μM cation-anion mixed solution, the electric potential at which an extraction efficiency of 95% or more is obtained for all of the ions was 10 V.

(Evaluation 3-2)

Figure 11:
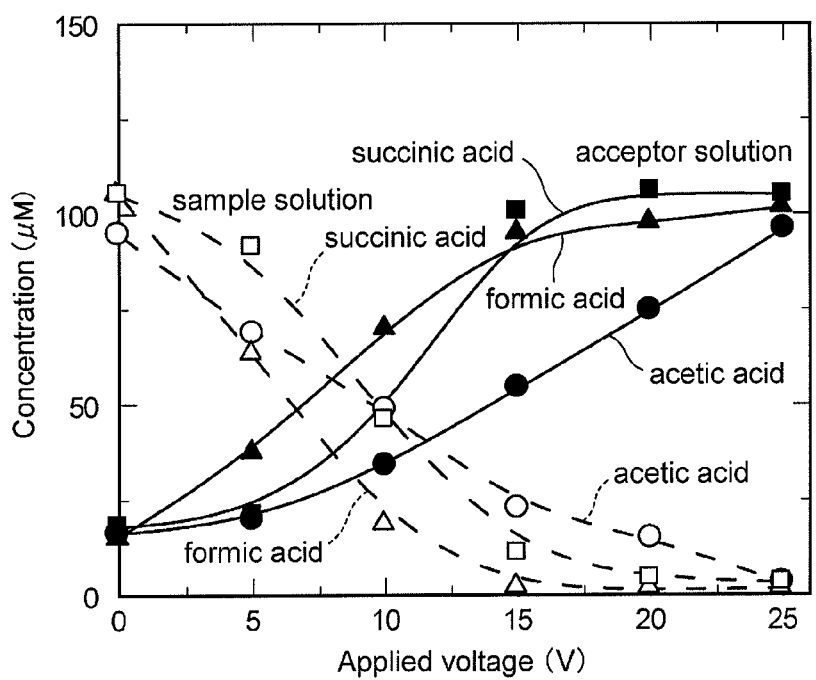
FIG. 11 is a view showing a result of evaluation when representative organic acid standard solutions (concentration of 100 μM) are used as a sample solution by using dissolved ion analysis system provided with Example 3 (pretreatment device 1D (flat plate lamination type)).

FIG. 11 shows a result of evaluation by using a standard solution (concentration of 100 μM) of formic acid (HCOOH), acetic acid ($CH_3COOH$), and succinic acid (($CH_2COOH)_2$), which are representative organic acids, as a sample solution while using the dissolved ion analysis system 20 having the aforementioned construction.

Here, the evaluation conditions were similar to those of the above (Evaluation 3-1) except that a 10 mM phosphoric acid buffer solution (pH 7.0) was used as the acceptor solution of the acceptor solution flow channel 13b.

As will be shown in FIG. 11, the extraction amount of formic acid, acetic acid, and succinic acid, which are organic acid ions, increased according as the applied voltage increased, in the same manner as the inorganic ions. From this result, it has been found out that an organic acid ion of 100 μM can be quantitatively extracted.

(Evaluation 3-3)

By using the dissolved ion analysis system 20 having the above-described construction, a mineral water sample and a urine sample were measured as real samples.

With respect to the results, Table 1 shows a result of evaluation of a service water sample, and Table 2 shows a result of evaluation of a urine sample. Here, since the urine sample exceeds a quantification range by an ion chromatograph, the urine sample was measured after being diluted by 100 times.

TABLE 1

| Mineral water sample | Dissolved ion | | | | | | |
|---|---|---|---|---|---|---|---|
| | $Na^+$ | $NH_4^+$ | $K^+$ | $Ca^{2+}$ | $Br^-$ | $NO_3^-$ | $SO_4^{2-}$ |
| Sample concentration (mM) | 458 | 26.4 | 127 | 337 | 1.14 | 154 | 144 |
| Concentration in extraction water (mM) | 484 | 11.5 | 125 | 322 | 1.38 | 153 | 144 |
| Relative standard deviation (%) | 2.5 | 2.6 | 2.8 | 2.2 | 8.4 | 0.7 | 0.9 |

TABLE 2

| Urine sample (diluted by 100 times) | Dissolved ion | | | | | | |
|---|---|---|---|---|---|---|---|
| | $Na^+$ | $NH_4^+$ | $K^+$ | $Ca^{2+}$ | $Br^-$ | $NO_3^-$ | $SO_4^{2-}$ |
| Sample concentration (mM) | 3879 | 371 | 416 | 106 | 1.12 | 32.3 | 150 |
| Concentration in extraction water (mM) | 4060 | 329 | 412 | 113 | 1.24 | 33.1 | 151 |
| Relative standard deviation (%) | 1.4 | 4.8 | 5 | 3.8 | 5.8 | 3.1 | 1.9 |

From Table 1 and Table 2, it has been confirmed that, with respect to both the mineral water sample and the urine sample, the value measured by using the pretreatment device of the present invention and the value measured by performing a pretreatment using a conventional filter (manufactured by Millipore Co., Ltd., MIREX HN syringe filter, diameter of 33 mm, pore diameter of 0.45 μm) were extremely close to each other, so that the pretreatment device of the present invention is effective also for real samples.

The reproducibility by repetitive measurement for 10 times was 2.9±2.4% in the case of the mineral water sample, and the reproducibility by repetitive measurement for 10 times was 3.6±1.5% in the case of the urine sample.

Example 4

Flat Plate Lamination Type Pretreatment Device (Five Solution Layers), Modified Cellulose Permeation Membrane By using dissolved ion analysis system 10 that accords to the construction shown in FIG. 1, an experiment of extracting dissolved ions contained in a sample solution was conducted. As the pretreatment device, the pretreatment device 1D of a flat plate lamination type (five solution layers) was used.

The construction of the pretreatment device 1B in the dissolved ion analysis system 10 that was actually put to use is as follows. Here, as the sample solution supplying means 2, the pure water supplying means 3, and the analyzing means 4 besides that, the same apparatuses as those in the Example 1 were used, and a peristaltic pump was used for solution transportation to the feed solution supplying flow channel 16.

"Pretreatment Device 1D"

Electrode 14a (positive electrode): platinum plated mesh

Dialysis membrane 12a: regenerated cellulose membrane (manufactured by

Spectrum-Laboratories Co., Ltd., Type: 129020, thickness: 18 μm, molecular weight cut off (MWCO): 8000) modified by a method described later Dialysis membrane 12b: regenerated cellulose membrane (manufactured by Spectrum-Laboratories Co., Ltd., Type: 129020, thickness: 18 μm, molecular weight cut off (MWCO): 8000)

Electrode diaphragm 15a: manufactured by AGC Engineering Co., Ltd., SELEMION (registered trademark) CMV, thickness 130 μm (cation exchange membrane)

Electrode diaphragm 15b: manufactured by AGC Engineering Co., Ltd., SELEMION (registered trademark) DSV, thickness 100 μm (anion exchange membrane)

Electrode 14b (negative electrode): platinum plated mesh

The sizes of the sample solution flow channel 11, the acceptor solution flow channel 13, and the feed solution supplying flow channel 16 in the pretreatment devices 1B having the above-described construction are as follows.

Sample solution flow channel 11: width 5 mm, length 40 mm, thickness 127 μm Acceptor solution flow channel 13: width 5 mm, length 40 mm, thickness 127 μm Feed solution supplying flow channel 16: width 5 mm, length 40 mm, thickness 127 μm <Method of Modifying Regenerated Cellulose Membrane>

The following chemical modification was carried out as the regenerated cellulose membrane of the dialysis membrane 12.

A regenerated cellulose membrane was immersed into pure water for 3 days and thereafter squeezed with filter paper to remove the moisture. Subsequently, after cleaning with methanol and acetone in this order, reduced-pressure drying was carried out for 24 hours to remove the solvent. Subsequently, the regenerated cellulose membrane was immersed into a 2 g/L aqueous solution of $NH_4SO_4Fe(II)$ at 30° C. for 30 minutes, and thereafter immersed into a 40 wt % Acrylic Acid 2-(Trimethylamino)ethyl Ester (hereafter referred to as "TMAEA-Qc1"), 2 mM $H_2O_2$ aqueous solution, at 50° C. for 10 hours after removing dissolved oxygen by nitrogen substitution.

Figure 12:
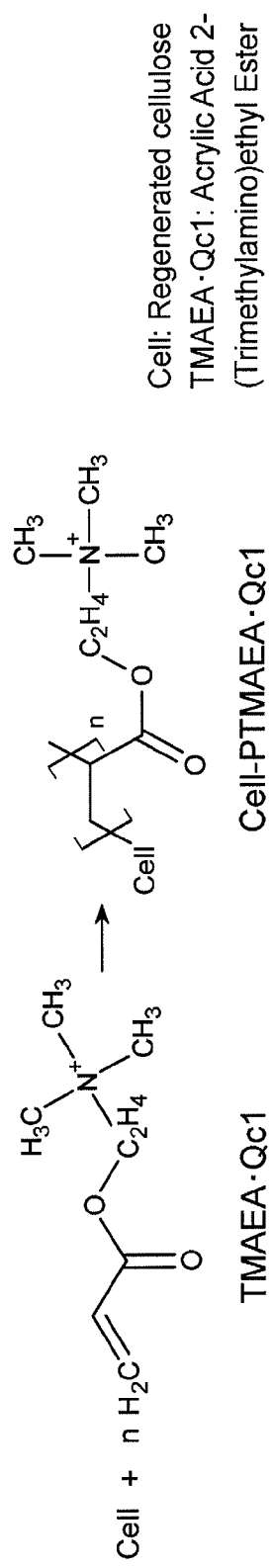
FIG. 12 is a reaction scheme of regenerated cellulose and TMAEA-Qc1.

The regenerated cellulose membrane subjected to the aforementioned treatment was subjected to a deironation treatment in a 1 wt % aqueous solution of oxalic acid, and thereafter cleaning with hot water and cleaning with water were repetitively carried out to remove the unreacted substances. Thereafter, the regenerated cellulose membrane subjected to reduced-pressure drying was cleaned with a 10 mM aqueous solution of HCl and with a 10 mM aqueous solution of NaOH in this order, and cleaning with hot water and cleaning with water were repetitively carried out to remove the chemical solution. Thereafter, reduced-pressure drying was carried out for 24 hours to obtain a modified regenerated cellulose membrane modified with a polymer of TMAEA-Qc1 (PTMAEA-Qc1) having a positive electric charge. FIG. 12 shows a reaction scheme of regenerated cellulose and TMAEA-Qc1.

(Evaluation 4-1)

Pretreatment devices 1D in which the above-described modified regenerated cellulose membrane was used as the dialysis membrane 12a and in which a regenerated cellulose membrane not yet modified (Normal) was used as a dialysis membrane 12a' for comparison were respectively fabricated.

As the sample solution, a mixed solution of ions, containing a cation ($K^+$) and an anion ($NO_3^-$) respectively at 100 μM, was used.

The mixed solution of ions was allowed to flow through the sample solution flow channel 11 under conditions with a flow rate of 300 μL/min, and pure water was allowed to flow through the channel acceptor solution flow channel 13 and the feed solution supplying flow channel 16 under conditions with flow rates of 300 μL/min and 300 μL/min, respectively. In this state, a voltage was applied between the electrodes 14a, 14b from the direct current power source 5. The introduced sample solution and extraction solution were captured respectively at exits of the device and were quantitated with an ion chromatograph to evaluate the characteristics of the migration membrane extraction.

Figure 13:
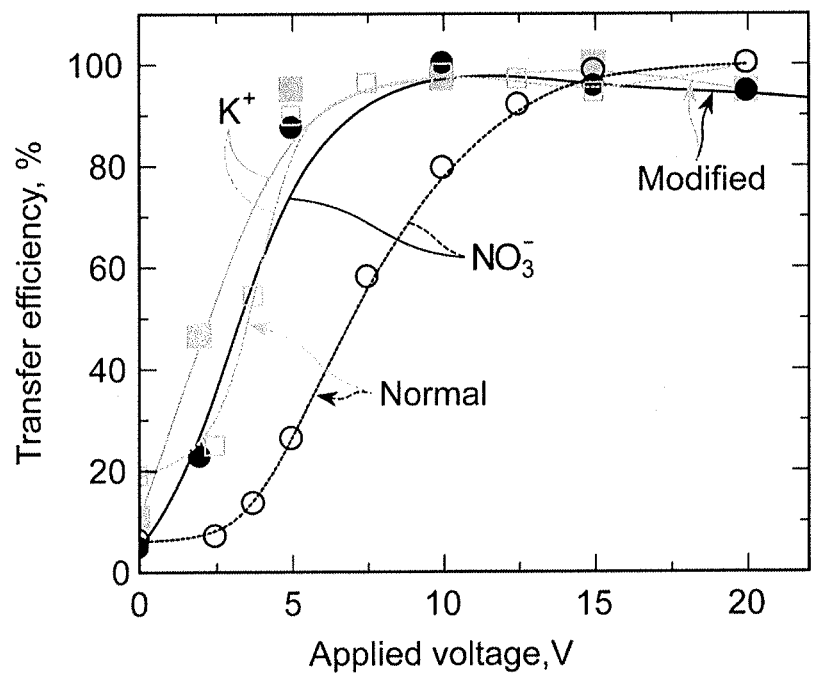
FIG. 13 is a view showing a relationship between an applied voltage and an effect of extracting dissolved ions when a modified regenerated cellulose membrane is used as a dialysis membrane in Example 4 (pretreatment device 1D (flat plate lamination type)).

FIG. 13 shows a relationship between the applied voltage and the effect of extracting the dissolved ions when the respective ion permeation membranes were used.

As shown in FIG. 13, with the modified regenerated cellulose membrane, the applied voltage needed for quantitative permeation of an anion ($NO_3^-$) was definitely smaller as compared with the regenerated cellulose membrane not yet modified, and was approximately equal to that of cations. From this fact, it has been confirmed that the modified regenerated cellulose membrane modified with a compound having a positive electric charge is suitable for separation of anions.

Example 5

Flat Plate Lamination Type Pretreatment Device (Five Solution Layers)

(Evaluation 5-1)

The following experiment was conducted with an apparatus construction similar to that of the Example 4.

As the sample solution, a cation-anion mixed solution containing two kinds of cations ($Li^+$, $K^-$) and four kinds of anions ($CH_3SO_3^-$, $Br^-$, $NO_3^-$, $SO_4^{2-}$) respectively at 10 μM was used.

The mixed solution of ions was allowed to flow through the sample solution flow channel 11 under conditions with a flow rate of 100 to 3000 μL/min in concentrating and under conditions with a flow rate of 50 μL/min in diluting. Pure water was respectively supplied to the channel acceptor solution flow channels 13a, 13b at a flow rate of 100 μL/min in concentrating and at a flow rate of 3000 to 50 μL/min in diluting. Also, pure water was supplied to the feed solution supplying flow channels 16a, 16b at a flow rate of 300 μL/min. In this state, a voltage of 35 V was applied between the electrodes 14a, 14b from the direct current power source 5. The introduced sample solution and extraction solution were captured respectively at exits of the device and were quantitated with an ion chromatograph to determine the concentration ratio.

Figure 14:
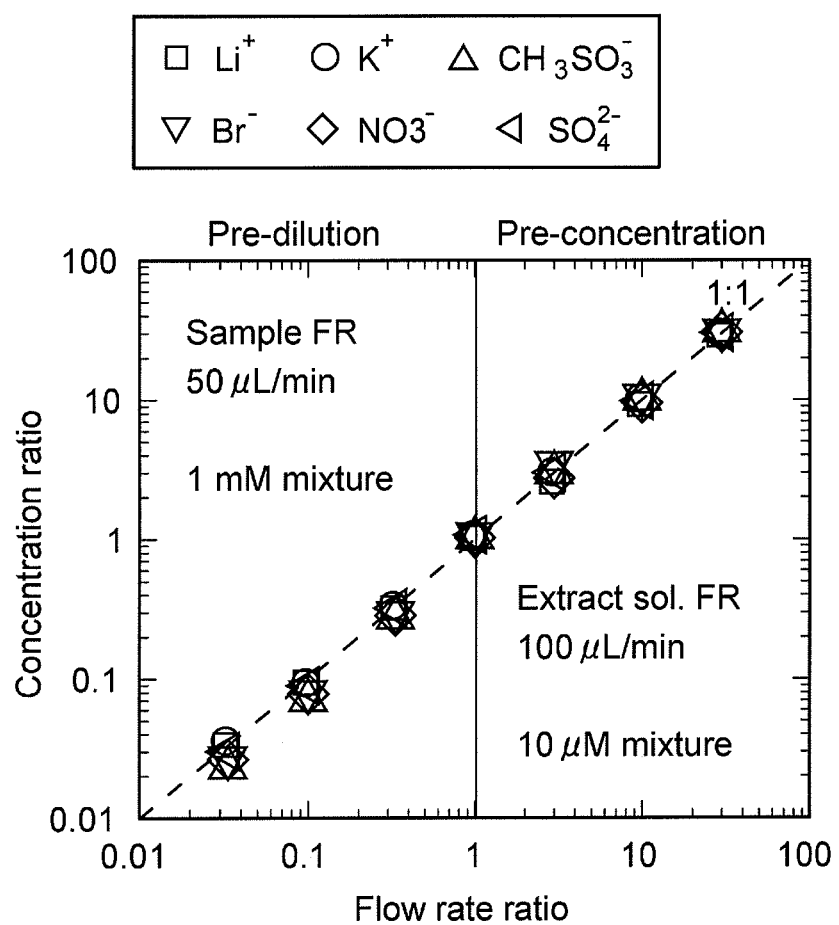
FIG. 14 is a view showing a relationship between the flow rate ratio (sample solution/extraction solution) and the concentration ratio (ion concentration obtained in the acceptor solution/sample concentration).

The result is shown in FIG. 14. When the flow rate ratio (sample flow rate/extraction solution flow rate) was larger than 1, the ion components were obtained at a higher concentration in the extraction solution than in the sample solution, whereas when the flow rate ratio was smaller than 1, the ion components were obtained at a lower concentration in the extraction solution than in the sample solution. At this time, a relationship of being equal was obtained between the concentration of the ion components in the sample solution and the concentration of the ion components in the acceptor solution. From this fact, the ions in the sample could be obtained in the acceptor solution by being concentrated or diluted at a concentration ratio corresponding to the flow rate ratio of the sample solution and the acceptor solution simultaneously with the pretreatment of the measurement sample.

(Evaluation 5-2)

Figure 15:
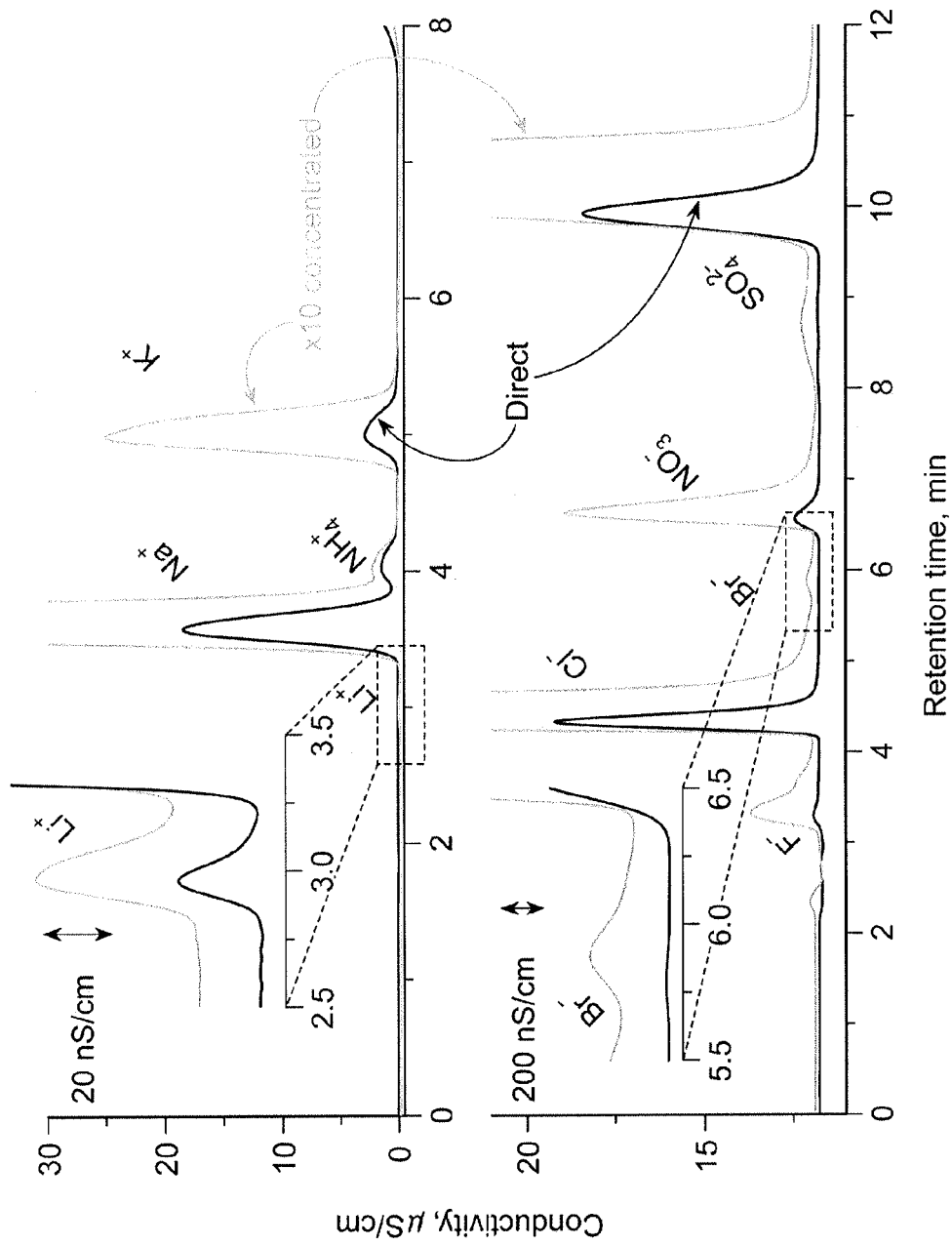
FIG. 15 is a result of measurement by in-line concentration of service water.

By using the dissolved ion analysis system 20 having the above-described construction, measurement of service water by pretreatment with simultaneous concentration was carried out. Here, the flow rate of the sample solution was set to be 1000 µL/min, and the flow rate of the acceptor solution was set to be 100 µL/min. The obtained chromatogram is shown in FIG. 15. Both in the case of cations and in the case of anions, a peak height 10 times as large as that (Direct) obtained when the sample was directly introduced into the ion chromatograph for comparison was obtained. In particular, the quantification property of $Li^+$ ion and $Br^-$ ion contained in slight amounts in service water was found to be greatly improved.

INDUSTRIAL APPLICABILITY

The present invention can be suitably applied to the field of environment analysis or quality management in which a routine analysis is carried out, real time monitoring of a living body sample, or the like.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims. No. 2010-268404 filed on Dec. 1, 2010

The entire disclosure of Japanese Patent Application including specification, claims, drawings and summary is incorporated herein by reference in its entirety.

DESCRIPTION OF REFERENCE SYMBOLS 1A, 1B, 1C, 1D pretreatment device
2 sample solution supplying means
3 pure water supplying means
4, 4a, 4b analyzing means
5 direct current power source
10, 20 dissolved ion analysis system
11 sample solution flow channel
12, 12a, 12b dialysis membrane
13, 13a, 13b acceptor solution flow channel
14a, 14b electrode
15, 15a, 15b electrode diaphragm
16, 16a, 16b feed liquid supplying flow channel

The invention claimed is:

1. A pretreatment device for analysis of dissolved ions, comprising:
   a sample solution flow channel through which a sample solution containing dissolved analyte ions flows;
   an acceptor solution flow channel which is arranged adjacent to the sample solution flow channel so as to intercalate a dialysis membrane between the acceptor solution flow channel and the sample solution flow channel;
   a pair of electrodes which are so arranged as to intercalate the sample solution flow channel and the acceptor solution flow channel therebetween, wherein one of the pair of electrodes is provided on the sample solution flow channel, and the other one of the pair of electrodes is provided on the acceptor solution flow channel;
   a direct current power source which enables the generation of a predetermined potential difference between the electrodes; and
   an electrode separator which is provided between the dialysis membrane and an inside surface of the electrode provided on the acceptor solution flow channel.

2. The pretreatment device for analysis of dissolved ions according to claim 1, wherein the dialysis membrane has a molecular weight cut off of 2000 to 15000.

3. The pretreatment device for analysis of dissolved ions according to claim 1, wherein the dialysis membrane is a cellulose dialysis membrane.

4. The pretreatment device for analysis of dissolved ions according to claim 3, wherein the cellulose constituting the cellulose dialysis membrane is chemically modified by a modification compound.

5. The pretreatment device for analysis of dissolved ions according to claim 4, wherein the modification compound is a compound having an electric charge.

6. The pretreatment device for analysis of dissolved ions according to claim 4, wherein the modification compound is a compound having a small interaction to a biological component.

7. The pretreatment device for analysis of dissolved ions according to claim 1, wherein the electrode separator is an ion exchange membrane or a bipolar membrane.

8. The pretreatment device for analysis of dissolved ions according to claim 1, wherein the acceptor solution flow channel is provided on both sides of the sample solution flow channel so as to intercalate the sample solution flow channel therebetween.

9. A dissolved ion analysis system having:
   the pretreatment device for analysis of dissolved ions according to claim 1;
   a sample solution supplying means for supplying the sample solution to the sample solution flow channel of the pretreatment device;
   an acceptor solution supplying means for supplying an acceptor solution to the acceptor solution flow channel of the pretreatment device; and
   an analyzing means for analyzing the dissolved ions contained in the acceptor solution discharged by passing through the acceptor solution flow channel of the pretreatment device.

* * * * *